United States Patent
Kaneko

(10) Patent No.: US 11,470,810 B2
(45) Date of Patent: Oct. 18, 2022

(54) TOILET FOR ANIMAL

(71) Applicant: UNICHARM CORPORATION, Shikokuchuo (JP)

(72) Inventor: Shinya Kaneko, Kagawa (JP)

(73) Assignee: UNICHARM CORPORATION, Ehime (JP)

(*) Notice: Subject to any disclaimer, the term of this patent is extended or adjusted under 35 U.S.C. 154(b) by 51 days.

(21) Appl. No.: 16/908,741

(22) Filed: Jun. 23, 2020

(65) Prior Publication Data
US 2020/0315125 A1     Oct. 8, 2020

Related U.S. Application Data

(63) Continuation of application No. 16/060,965, filed as application No. PCT/JP2016/076759 on Sep. 12, 2016, now Pat. No. 10,729,097.

(30) Foreign Application Priority Data

Dec. 25, 2015  (JP) .............................. JP2015-253029

(51) Int. Cl.
| | | |
|---|---|---|
| *A01K 1/01* | (2006.01) | |
| *A01K 29/00* | (2006.01) | |
| *A61B 5/20* | (2006.01) | |
| *A01K 23/00* | (2006.01) | |

(52) U.S. Cl.
CPC .............. *A01K 1/0114* (2013.01); *A01K 1/01* (2013.01); *A01K 29/00* (2013.01); *A61B 5/208* (2013.01); *A01K 23/005* (2013.01); *A61B 2503/40* (2013.01)

(58) Field of Classification Search
CPC .... A01K 1/011; A01K 1/0114; A01K 1/0107; A01K 29/005; A01K 23/005; A01K 1/031; A01K 1/01; A61B 5/207
USPC ......................... 119/161, 163, 165, 166, 169
See application file for complete search history.

(56) References Cited

U.S. PATENT DOCUMENTS

| | | |
|---|---|---|
| 5,596,948 A | 1/1997 | Ritchie |
| 7,017,519 B1 | 3/2006 | Deasy et al. |
| 7,905,201 B2 | 3/2011 | Greene et al. |

(Continued)

FOREIGN PATENT DOCUMENTS

| | | |
|---|---|---|
| CN | 102472740 A | 5/2012 |
| JP | 2006226919 A | 8/2006 |

(Continued)

OTHER PUBLICATIONS

Office Action in CN Application No. 201680076171.X, dated Jun. 1, 2021, 8pp.

(Continued)

*Primary Examiner* — Yvonne R Abbott-Lewis
(74) *Attorney, Agent, or Firm* — Hauptman Ham, LLP

(57) ABSTRACT

A toilet for animal, including: an upper container having a plurality of holes formed on a bottom portion, the plurality of holes penetrating in an up-down direction; a lower container that includes a receiving section receiving excrement that has passed through the plurality of holes, gravity of the upper container not acting on the lower container; and an output unit that outputs a signal changing according to an amount of the excrement received by the receiving section.

12 Claims, 8 Drawing Sheets

(56) References Cited

U.S. PATENT DOCUMENTS

| | | | |
|---|---|---|---|
| 8,464,662 B1 * | 6/2013 | Shorenstein | A01K 1/0107 119/164 |
| 2009/0241850 A1 * | 10/2009 | Campbell | A01K 1/0117 119/164 |
| 2011/0120383 A1 | 5/2011 | Greene et al. | |
| 2012/0137758 A1 | 6/2012 | Mizumachi et al. | |
| 2012/0299731 A1 | 11/2012 | Triener | |
| 2013/0171597 A1 | 7/2013 | Kong | |
| 2018/0242889 A1 | 8/2018 | Izumo et al. | |
| 2019/0191660 A1 | 6/2019 | Takada et al. | |
| 2019/0364840 A1 | 12/2019 | Baxter et al. | |
| 2020/0060221 A1 * | 2/2020 | Fan | A01K 1/0114 |

FOREIGN PATENT DOCUMENTS

| | | |
|---|---|---|
| JP | 2007330200 A | 12/2007 |
| JP | 2009153409 A | 7/2009 |
| JP | 2014236683 A | 12/2014 |
| JP | 5699082 B2 | 4/2015 |
| JP | 6441532 B1 | 12/2018 |
| JP | 202072751 A | 5/2020 |
| TW | I386159 B1 | 2/2013 |
| WO | 2014196418 A1 | 12/2014 |
| WO | 2017104216 A1 | 6/2017 |

OTHER PUBLICATIONS

International Search Report in PCT Application No. PCT/JP2016/076759, dated Dec. 6, 2016, 4pp.
International Preliminary Report on Patentability in PCT Application No. PCT/JP2016/076759, dated Dec. 6, 2016, 9pp.
Extended European Search Report in EP Application No. 16878058.3, dated Sep. 27, 2018, 8pp.
Office Action in JP Application No. 2018-112699, dated Nov. 12, 2019, 2pp.
Office Action in TW Application No. 105134576 dated Nov. 29, 2019, 3pp.
Office Action in JP Application No. 2020-022392, dated Jan. 19, 2021, 3pp.
Office Action in CN Application No. 201680076171.X, dated Aug. 4, 2020, 8pp.
Office Action in AU Application No. 2016376509, dated Apr. 13, 2021, 7pp.
Office Action in EP Application No. 16878058.3, dated Dec. 23, 2021, 6pp.
Office Action in JP application No. 2021-149679, dated Aug. 23, 2022, 2pp.

* cited by examiner

TOILET FOR ANIMAL

RELATED APPLICATIONS

The present application is a continuation application of U.S. application Ser. No. 16/060,965, filed Jun. 11, 2018, which is a national phase of International Application Number PCT/JP2016/076759, filed Sep. 12, 2016, which claims priority to Japanese Application Number 2015-253029, filed Dec. 25, 2015, the disclosures of which applications are hereby incorporated by reference herein in their entirety.

TECHNICAL FIELD

The present invention relates to a toilet for animal.

BACKGROUND ART

A toilet used by an animal such as a cat reared indoors is conventionally known as a toilet for animal. A toilet configured to measure the number of excretions of the animal is also known as such a toilet for animal (for example, see PTL 1).

CITATION LIST

Patent Literature

[PTL 1] Japanese Unexamined Patent Application Publication No. 2009-153409

SUMMARY OF INVENTION

Technical Problem

A toilet described in PTL 1 is capable of measuring the number of excretions, but incapable of measuring an amount of excrement (for example, an amount of urine). In view of this, it was difficult to early detect a disease (for example, chronic renal failure) whose symptom appears in the amount of urine, and to determine a replacement timing of an absorbent sheet that absorbs the urine.

The present invention has been made in consideration of the problem as described above. An object of the present invention is to provide a toilet for animal that is capable of measuring an amount of excrement.

Solution to Problem

A principal aspect of the present invention to achieve the above advantage is a toilet for animal, including: an upper container having a plurality of holes formed on a bottom portion, the plurality of holes penetrating in an up-down direction; a lower container that includes a receiving section receiving excrement that has passed through the plurality of holes, gravity of the upper container not acting on the lower container; and an output unit that outputs a signal changing according to an amount of the excrement received by the receiving section. Other features of the present invention will be made clear through the present specification with reference to the accompanying drawings.

Advantageous Effects of Invention

The present invention is capable of measuring the amount of excrement.

DESCRIPTION OF EMBODIMENTS

Figure 1:
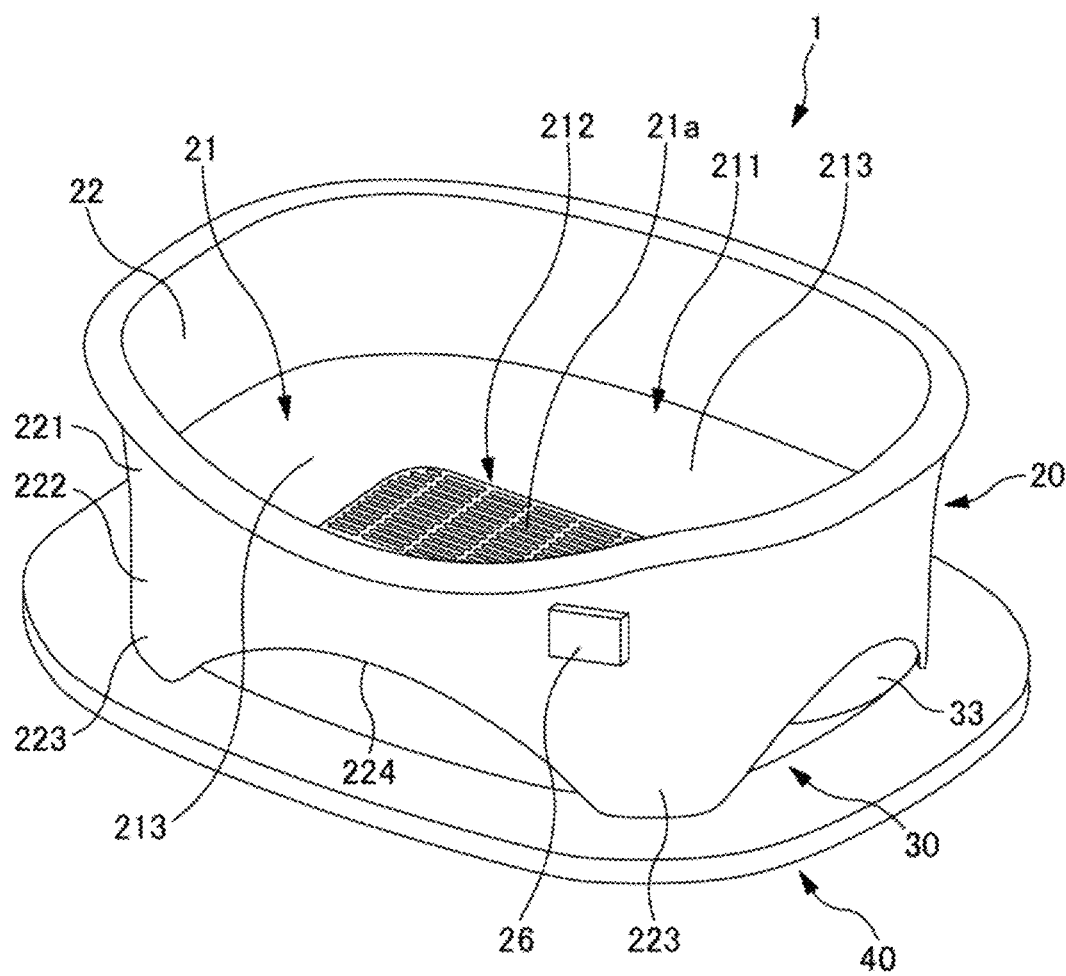
FIG. 1 is a perspective view illustrating a toilet for animal 1 according to a first embodiment of the present invention.

At least the following matters will be made clear by the description in the present specification and the accompanying drawings.

Disclosed is a toilet for animal, including: an upper container having a plurality of holes formed on a bottom portion, the plurality of holes penetrating in an up-down direction; a lower container that includes a receiving section receiving excrement that has passed through the plurality of holes, gravity of the upper container not acting on the lower container; and an output unit that outputs a signal changing according to an amount of the excrement received by the receiving section.

According to such a toilet for animal, only the excrement (urine) that has passed through the plurality of holes falls in the receiving section of the lower container. This can measure the amount of this excrement (amount of urine) based on the signal output from the output unit.

In this toilet for animal, it is preferable that an absorbent sheet that absorbs the excrement is placed on the receiving section.

Such a toilet for animal facilitates determination of a replacement timing of the absorbent sheet.

In this toilet for animal, it is preferable that the toilet for animal further includes a support member that supports the lower container, and the output unit is disposed on the support member and located below the lower container.

Such a toilet for animal is capable of measuring the amount of the excrement based on a force that the output unit receives from the lower container.

In this toilet for animal, it is preferable that the lower container includes an engaging section that is engageable with the output unit.

Such a toilet for animal is capable of reducing positional deviation and bias between the lower container and the support member.

In this toilet for animal, it is preferable that the output unit is waterproof.

With such a toilet for animal, the support member is washable with water.

In this toilet for animal, it is preferable that the support member includes a control unit that detects an amount of the excrement based on the signal outputted from the output unit.

With such a toilet for animal, only the toilet for animal is capable of measuring the amount of the excrement without using another member (such as an external terminal).

In this toilet for animal, it is preferable that the control unit detects an amount of the excrement each time by calculating a difference between a signal outputted before excretion and a signal outputted after excretion.

Such a toilet for animal is capable of enhancing a measurement accuracy of the amount of the excrement.

In this toilet for animal, it is preferable that the upper container includes water-repellent, liquid-permeable particles, and when detecting an amount of the excrement, the control unit adds a correction value that is set for the liquid-permeable particles in advance.

Such a toilet for animal is capable of further enhancing the measurement accuracy of the amount of the excrement.

In this toilet for animal, it is preferable that the upper container includes a display section that displays a result of detection detected by the control unit, and the control unit is capable of communicating with the display section by radio.

Such a toilet for animal improves visibility of the result of detection.

In this toilet for animal, it is preferable that the toilet for animal further includes an upper-container output unit that outputs an upper-container weight signal, the upper-container weight signal changing according to a weight of the upper container.

Such a toilet for animal is capable of increasing the measurement objects.

In this toilet for animal, it is preferable that the toilet for animal further includes an upper-container control unit that detects, based on the upper-container weight signal, at least either one of an weight of an animal and an amount of excrement that has not passed through the plurality of holes.

Such a toilet for animal is capable of measuring the weight of the animal and the amount of solid excrement (feces).

In this toilet for animal, it is preferable that the toilet for animal further includes a battery for supplying electrical power.

Such a toilet for animal ensures improvement in safety.

First Embodiment

A toilet for animal according to embodiments of the present invention is used by an animal such as a cat, for example, reared indoors. The "animal" in this description includes not only a so-called pet such as a cat, a dog, a rabbit, and a hamster, but also, for example, babies of a tiger and a lion.

<Overall Configuration of Toilet for Animal 1>

A description will be given of a configuration of a toilet for animal 1 with reference to FIG. 1 to FIG. 5. In the following description, a normal direction of a surface of a floor plate 40 is set to an up-down direction. A side where an upper container 20 and a lower container 30 are located with respect to the floor plate 40 is set to "up", and its opposite side (floor side) is set to "down".

Figure 2:
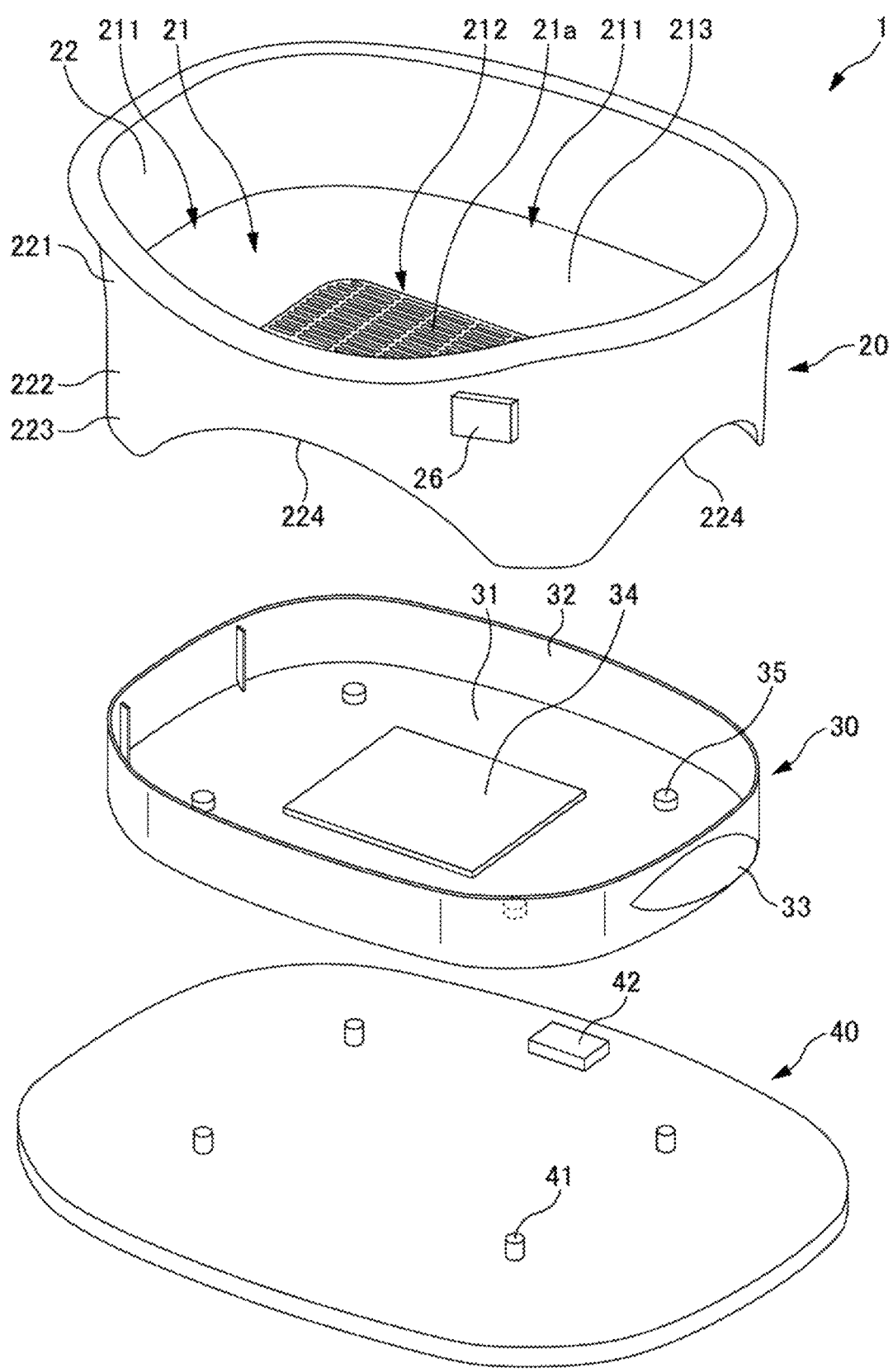
FIG. 2 is an exploded explanatory view of the toilet for animal 1.
Figure 3:
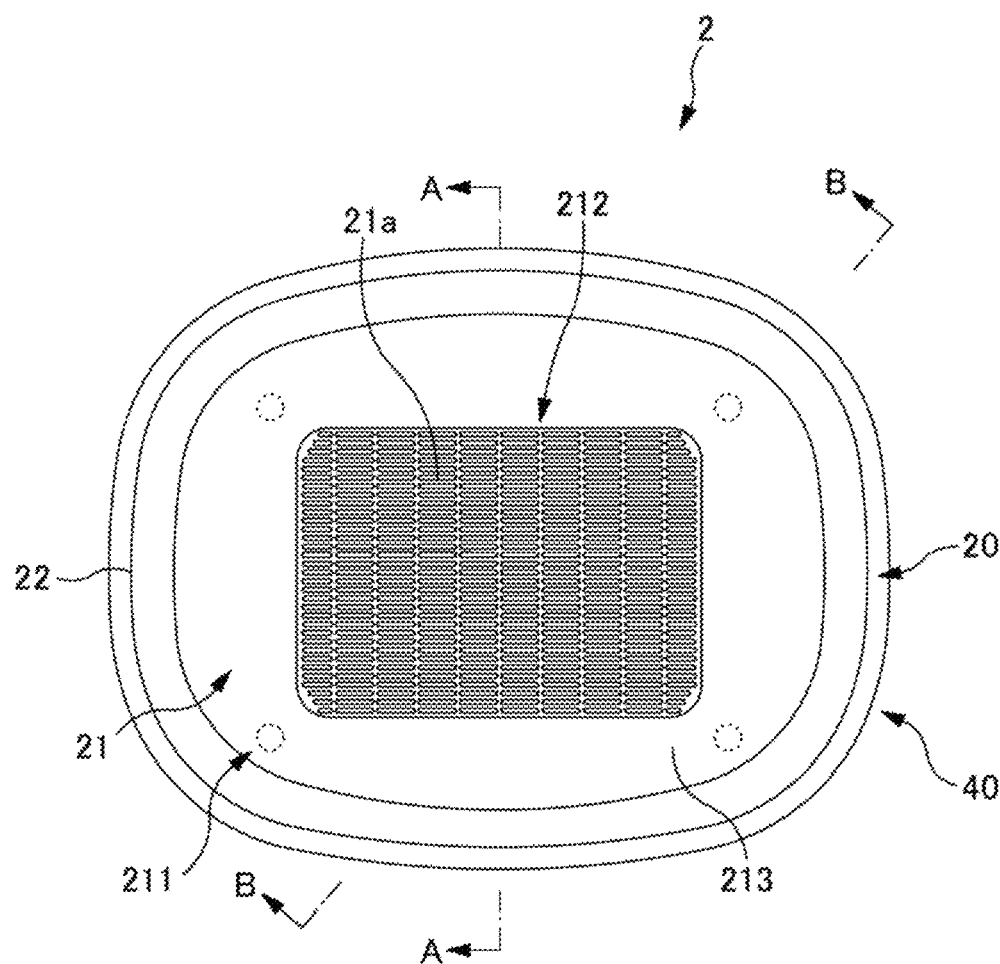
FIG. 3 is a view when the toilet for animal 1 is viewed from above.
Figure 4:
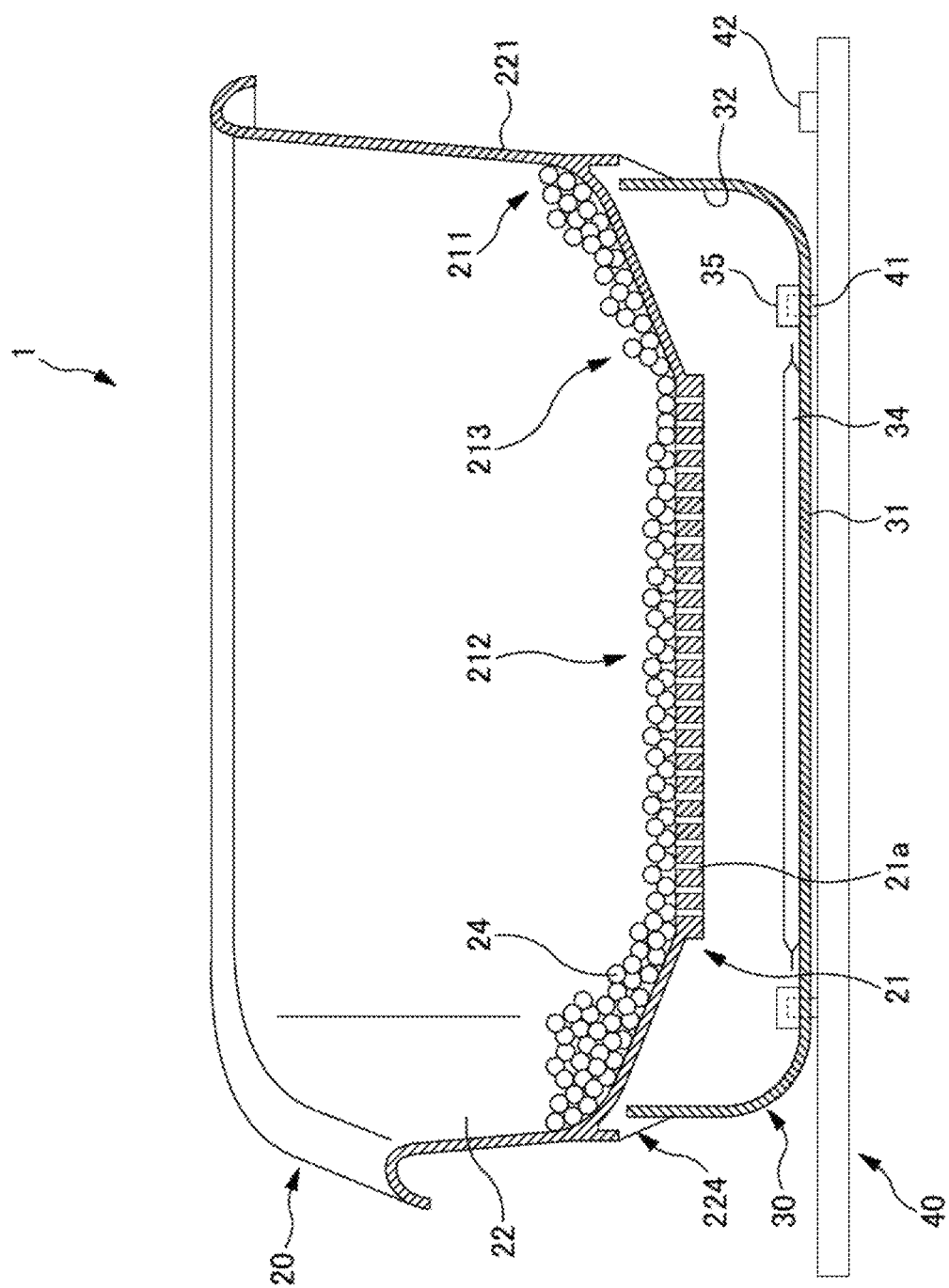
FIG. 4 is a cross-sectional view taken along a line A-A of FIG. 3.
Figure 5:
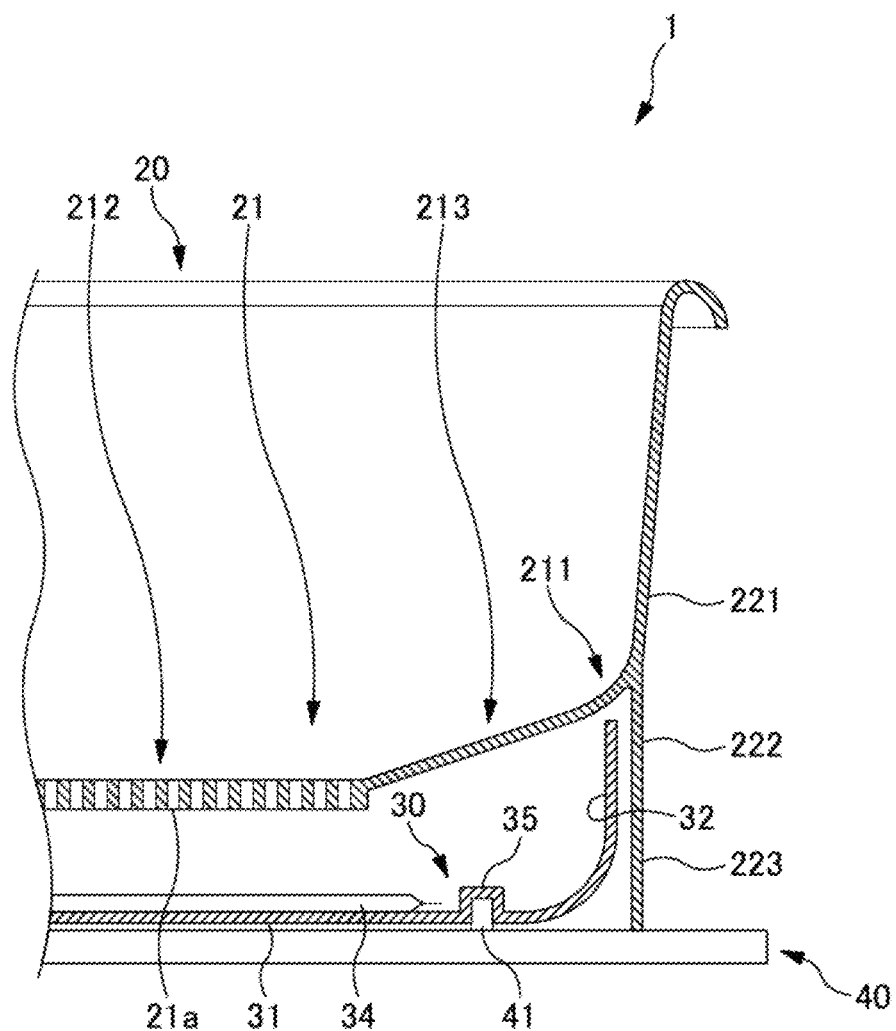
FIG. 5 is a cross-sectional view taken along a line B-B of FIG. 3.

FIG. 1 is a perspective view illustrating the toilet for animal 1 according to a first embodiment of the present invention. FIG. 2 is an exploded explanatory view of the toilet for animal 1. FIG. 3 is a view when the toilet for animal 1 is viewed from above. FIG. 4 is a cross-sectional view taken along a line A-A of FIG. 3. FIG. 5 is a cross-sectional view taken along a line B-B of FIG. 3. The drawings other than FIG. 4 illustrate a state where the upper container 20 does not house excrement treatment materials 24 (the excrement treatment material 24 is not illustrated).

The toilet for animal 1 includes the upper container 20, the lower container 30, and the floor plate 40 (equivalent to a support member). This toilet for animal 1 is, for example, used by being installed on an indoor floor or the like.

(Configuration of Upper Container 20)

The upper container 20, which is an open-topped container, has a bottom portion 21 and a sidewall portion 22.

As illustrated in FIG. 4, the bottom portion 21 has a peripheral edge portion 211, a plane surface portion 212, and a tapered surface portion 213.

The peripheral edge portion 211 is a part near an outer periphery of the bottom portion 21 in plan view.

The plane surface portion 212 is located on an approximate center of the bottom portion 21 in plan view, and located on a lowermost part of the bottom portion 21 in a height direction (up-down direction). The plane surface portion 212 is a surface of the upper container 20 extending in an approximately horizontal direction. A plurality of through-holes 21a are formed on the plane surface portion 212. Each through-hole 21a is formed into a size through which urine (liquid) passes, but feces (solid) does not pass, among excrement of the animal.

The tapered surface portion 213 is an acclivitous surface from a peripheral edge of the plane surface portion 212 toward the peripheral edge portion 211 of the bottom portion 21. That is, the tapered surface portion 213 is a declivitous surface from the peripheral edge portion 211 toward the approximate center. The tapered surface portion 213 has a taper angle that is preferably five degrees to 60 degrees with respect to the bottom portion 21. When the taper angle of the tapered surface portion 213 is too shallow to the extent falling below five degrees, it is difficult to move the urine or the like of the animal to a side of the plane surface portion 212 to guide it to the lower container 30. When the taper angle of the tapered surface portion 213 is too deep to the extent exceeding 60 degrees, a position on which the animal stably steps feet when stepping on the upper container 20 is narrow.

The sidewall portion 22 is a wall surface that is standing from the peripheral edge portion 211 of the bottom portion 21 and constitutes an outer wall of the upper container 20. The sidewall portion 22 has an upper wall portion 221 and an extending wall portion 222.

The upper wall portion 221 has a lower end continuous from an upper end of the tapered surface portion 213. Then, the upper wall portion 221 extends to an upper end portion of the upper container 20, and the upper wall portion 221 is warped outward at the upper end portion.

As illustrated in FIG. 5, the extending wall portion 222 is a part extending downward from the upper wall portion 221 on an outer surface side of the upper wall portion 221. As illustrated in FIG. 1 and FIG. 5, the extending wall portion 222 is located outside the lower container 30. The extending wall portion 222 extends to a top surface of the floor plate 40 to constitute foot portions 223 in four corners of the upper container 20. As illustrated in FIG. 1, the extending wall portion 222 has a cut-out portion 224 that is cut out so as to arc upward between the foot portion 223 and the foot portion 223.

As illustrated in FIG. 4, the upper container 20 houses the granular excrement treatment materials 24 (equivalent to liquid-permeable particles). Each of the excrement treatment materials 24 is a granular treatment material that absorbs or transmits liquid excrement of the animal such as the urine, and a so-called cat litter. In the present embodiment, a type that is water-repellent to transmit a lot of liquid to a liquid absorbent member is used as the excrement treatment material 24. This is because a type that absorbs the liquid, which absorbs urine, makes it difficult to accurately measure the amount of urine. However, the water-repellent treatment material also slightly absorbs the urine, and its amount is different depending on a kind of the excrement treatment material 24. Thus, in the present embodiment, as described below, when the amount of urine is detected, correction is carried out corresponding to the used excrement treatment material 24.

A display section 26 is disposed on the outer surface of the upper wall portion 221 of the upper container 20. The display section 26 is a part that displays output of a control unit 42 of the floor plate 40. The display section 26 includes, for example, a liquid crystal display. The display section 26 includes, for example, a communication unit (not illustrated) that communicates with the control unit 42 by radio, an input unit (not illustrated) for carrying out switching of a display content and various kinds of setting, and a battery (not illustrated) for supplying electrical power. Thus, the disposition of the display section 26 on the upper container 20 facilitates visibility of the display content. However, the disposition of the display section 26 is not limited to this. For example, the display section 26 may be disposed on the lower container 30 or the floor plate 40. When the display section 26 is disposed on the floor plate 40, the display section 26 may communicate with the control unit 42 by wire not by radio.

(Configuration of Lower Container 30)

As illustrated in FIG. 2, the lower container 30, which is an open-topped container, has a receiving section 31, a lower sidewall portion 32, and a handle portion 33.

The receiving section 31 is a part that receives the excrement (specifically, urine) that has passed through the plurality of through-holes 21a of the plane surface portion 212 of the upper container 20. An absorbent sheet 34 is located on this receiving section 31. The absorbent sheet 34 is a member configured to absorb the liquid excrement (urine) of the animal. The absorbent sheet 34 in the present embodiment is a square sheet foiled by stacking and bonding a liquid-permeable front surface sheet, a liquid-retaining interlayer sheet, and a liquid-non-permeable back side surface sheet.

An engaging section 35 is disposed on the receiving section 31. The engaging section 35 is a part engageable with a load cell 41 (described below) on the floor plate 40. The engaging section 35 is formed so as to project upward (such that a bottom surface is depressed). This engaging section 35 is disposed on a position corresponding to the load cell 41 of the floor plate 40.

The lower sidewall portion 32 is a wall standing from a peripheral edge of the receiving section 31. As illustrated in FIG. 4 and FIG. 5, in the toilet for animal 1 in the present embodiment, there is a clearance between an upper end of the lower sidewall portion 32 and the upper container 20 (peripheral edge portion 211). Thus, the lower sidewall portion 32 does not contact the upper container 20. Accordingly, gravity of the upper container 20 does not act on the lower container 30.

The handle portions 33 are located on an outer surface of the lower sidewall portion 32. The handle portions 33 are disposed on sides of the lower container 30 in a short side direction one by one. Thus, the handle positions 33 are disposed on total two positions facing one another. Each of the handle portion 33 is disposed so as to project outside the lower container 30.

(Configuration of Floor Plate 40)

The floor plate 40 is a plate-shaped member installed on the floor to support the upper container 20 and the lower container 30. In view of this, as illustrated in FIG. 1, the floor plate 40 is disposed having a size extending outside the foot portions 223 in the four corners of the upper container 20. However, it is only necessary that the floor plate 40 supports at least the lower container 30. That is, the floor plate 40 may be formed inside the foot portions 223 in the four corners of the upper container 20. In this case, the foot portions 223 of the upper container 20 will be located on the floor, and the upper container 20 will be supported to the floor.

As illustrated in FIG. 2, the load cell 41 and the control unit 42 are disposed on the floor plate 40.

The load cell 41 is a sensor that converts an applied force into an electrical signal to output it. The load cell 41 is disposed on the floor plate 40, and the load cell 41 is located below the lower container 30. In view of this, the load cell 41 outputs the signal corresponding to the force received from the lower container 30. In other words, the load cell 41 outputs the signal that changes according to the amount of the excrement received by the receiving section 31 of the lower container 30 (urine that has passed through the through-holes 21a). The load cell 41 in the present embodiment is a compression type having a circular cylindrical (columnar) shape. Four load cells 41 are located on the floor plate 40 at intervals. Then, the force is equally applied to these four load cells 41 from the lower container 30.

As illustrated in FIG. 4 and FIG. 5, each load cell 41 is engaged with the engaging section 35 of the lower container 30. This can reduce positional deviation and bias between the lower container 30 and the floor plate 40. As illustrated in FIG. 5, there is a clearance between a lower surface of the receiving section 31 of the lower container 30 and a top surface of the floor plate 40. Thus, gravity of the lower container 30 will act on only the load cell 41. The load cell 41 and the control unit 42 on the floor plate 40 are waterproof. This can separate the floor plate 40 the lower container 30 to wash the floor plate 40 with water.

The control unit 42 is coupled to the load cell 41 with a signal line (not illustrated). The control unit 42 detects the amount of urine based on the signal output from the load cell 41. As described above, the control unit 42 is capable of communicating with the display section 26 of the upper container 20 by radio. The control unit 42 causes the display section 26 to display a result of detection of the amount of urine.

Figure 6:
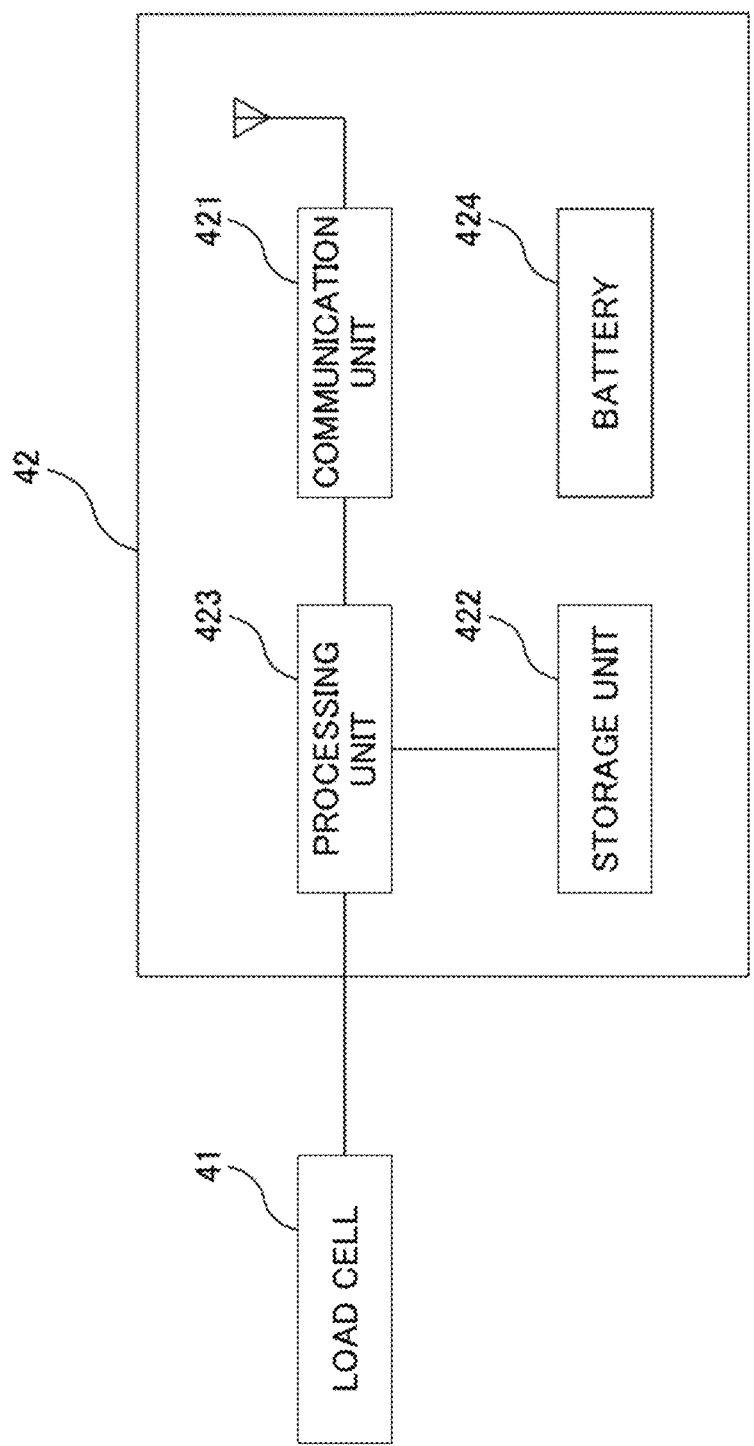
FIG. 6 is a block diagram illustrating a configuration of a control unit 42.

FIG. 6 is a block diagram illustrating an exemplary configuration of the control unit 42.

The control unit 42 includes a communication unit 421, a storage unit 422, a processing unit 423, and a battery 424.

The communication unit 421 is a site that communicates with a communication unit of the display section 26 by radio.

The storage unit 422 is constituted of a RAM, a ROM, and the like. The storage unit 422 is a site that stores various kinds of data and programs. The storage unit 422 in the present embodiment stores, for example, a program for detecting the amount of urine, a correction value associated with the excrement treatment material 24, detection result data of the amount of urine, and a threshold of the amount of urine each time.

The processing unit 423 is constituted of a CPU and the like. The processing unit 423 is a site that performs various kinds of arithmetic operation. For example, the processing unit 423 executes the program for detecting the amount of urine that is stored in the storage unit 422 to perform the arithmetic operation for detecting the amount of urine.

The battery 424 is a battery for supplying the electrical power to the respective sections (control unit 42, load cell 41) of the floor plate 40. In the present embodiment, a small-sized button battery is used as the battery 424. The battery 424 may be a disposable type battery (primary battery) or a battery that is a type repeatedly usable by being charged (secondary battery). The electrical power may be supplied from an external power supply such as a household outlet via a code without the battery 424. However, in this case, the animal possibly gets caught on the code or gets an electric shock. In contrast, the toilet for animal 1 in the present embodiment uses the battery 424, thus ensuring the improvement in safety.

In the present embodiment, the control unit 42 is disposed on the top surface of the floor plate 40. However, the disposition of the control unit 42 is not limited to this. For example, the control unit 42 may be disposed inside the floor plate 40. In this case, the battery 424 is preferably disposed separately from the control unit 42 (on a replaceable position).

<Operation for Measuring Amount of Urine by Toilet for Animal 1>

The following describes an operation for measuring the amount of urine by the toilet for animal 1.

First, the kind of the excrement treatment material 24 housed in the upper container 20 is preliminarily set. This setting can be carried out with an input unit (for example, a button) of the display section 26. Data showing the excrement treatment material 24 is transmitted from the display section 26 to the control unit 42 by radio to be received by the communication unit 421 of the control unit 42. The processing unit 423 of the control unit 42 refers to the storage unit 422 based on this data to set the correction value associated with the excrement treatment material 24 of the upper container 20.

When the animal such as the cat urinates on the bottom portion 21 of the upper container 20, this urine falls in the lower receiving section 31 of the lower container 30 through the clearance between the granular excrement treatment materials 24 and the through-holes 21a. The feces of the animal does not pass through the through-holes 21a, thus remaining on the bottom portion 21. That is, only the urine falls in the lower container 30. Then, the fallen urine is absorbed into the absorbent sheet 34 of the receiving section 31. This increases a weight of the absorbent sheet 34 (that is, increases the force that the load cell 41 receives from the lower container 30). Then, the load cell 41 outputs the signal corresponding to the force received from the lower container 30.

Figure 7:
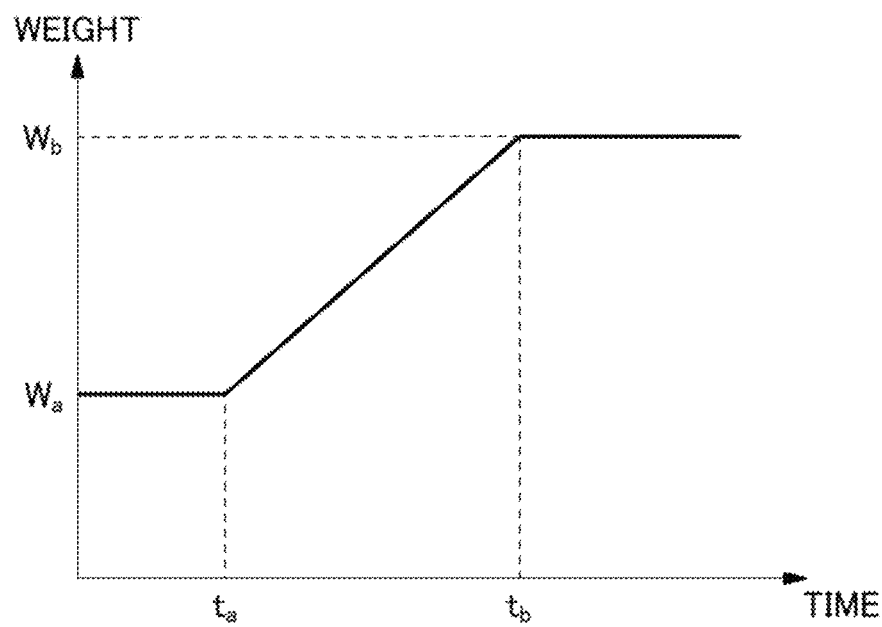
FIG. 7 is a view illustrating a time change of an output signal of a load cell 41.

FIG. 7 is a view illustrating an exemplary time change of the output signal of the load cell 41. FIG. 7 has a horizontal axis that shows a time and a vertical axis that shows a weight (amount corresponding to the output signal of the load cell 41).

The weight is approximately constant at Wa until a time ta. This weight Wa is an additional value obtained by adding a weight of the lower container 30 to the weight of the absorbent sheet 34 (also including the absorbed urine). When the weight thus does not change, the control unit 42 is in a standby mode (sleep mode). Immediately before the time ta, the animal comes to the toilet for animal 1 to urinate. In view of this, the urine falls in the receiving section 31 (absorbent sheet 34) of the lower container 30 at the time ta, and then, the weight starts increasing (the output signal of the load cell 41 changes). When the control unit 42 detects this change, the control unit 42 switches from the standby mode to a normal mode to start measuring the weight (amount of urine). The weight increases at an approximately constant rate between times ta and tb. Then, the weight becomes Wb at the time tb. Afterwards, the weight does not change (the output signal of the load cell 41 does not change). When the control unit 42 determines that the weight does not change for a predetermined period, the control unit 42 terminates the measurement of the weight.

Then, the processing unit 423 of the control unit 42 calculates a difference (Wb Wa) between the weight Wa when the weight starts increasing (the output signal of the load cell 41 before the urination) and the weight Wb when the increase of weight stops (the output signal of the load cell 41 after the urination). This difference corresponds to the amount of urine discharged by the urination each time.

The processing unit 423 adds the correction value preliminarily set with respect to the excrement treatment material 24 to the above-described difference. This ensures more accurate calculation of the amount of urine. Then, the control unit 42 causes the display section 26 of the upper container 20 to display the result of detection.

When the animal does not urinate for a while, the weight gradually decreases, for example, by water evaporation. However, when the animal urinates, the weight again increases. Also in this case, the difference between the output signal of the load cell 41 before the weight increases and the output signal of the load cell 41 when the increase stops is calculated. This can enhance the measurement accuracy of the amount of urine each time. The measurement accuracy of the amount of urine can be further enhanced by adding the correction value to this difference. The control unit 42 detects the amount of urine each time by this repetition of the calculation to cause the display section 26 to display it. This ensures early detection of a disease whose symptom appears in the amount of urine. For example, this ensures early detection of a chronic renal failure by which the amount of urine increases. The control unit 42 may compare the result of detection (amount of urine) each time with the threshold stored in the storage unit 422. Then, when the amount of urine exceeds the threshold, for example, it may be notified of the fact that it is abnormal by causing the display section 26 to emit light or by generating warning sound from a speaker (not illustrated) or the like. This facilitates detection of the abnormity.

The storage unit 422 stores the result of detection of the amount of urine each time. The processing unit 423 is also capable of calculating an accumulated amount of urine by accumulating the amount of urine each time with reference to the storage unit 422. The display section 26 in the present embodiment is also capable of displaying the accumulated amount of urine corresponding to setting (switching of the display content by the input unit). This facilitates determination of a replacement timing of the absorbent sheet 34. Physical condition management for animal can be also carried out by displaying a change history of the amount of urine.

As described above, the toilet for animal 1 in the present embodiment includes the upper container 20, the lower container 30, and the load cell 41. The upper container 20 has the bottom portion 21 on which the plurality of through-holes 21a penetrating in the up-down direction are formed. The lower container 30 has the receiving section 31 that receives the urine that has passed through the plurality of through-holes 21a. The gravity of the upper container 20 does not act on the lower container 30. The load cell 41 outputs the signal that changes according to the amount of urine received by the receiving section 31. This ensures measurement of only the amount of urine without confusing the weight of feces with the weight of urine. The measurement of the amount of urine facilitates the early detection of the disease (for example, chronic renal failure) whose symptom appears in the amount of urine and the determination of the replacement timing of the absorbent sheet 34 that absorbs the urine.

Second Embodiment

In a second embodiment, a weight of the upper container is also measured. This measurement ensures detection of a weight of the animal and the weight of feces. The following describes a toilet for animal 1 in the second embodiment with reference to the drawings. The same configurations as the first embodiment are denoted by the same reference numbers and the description thereof will be omitted.

Figure 8:
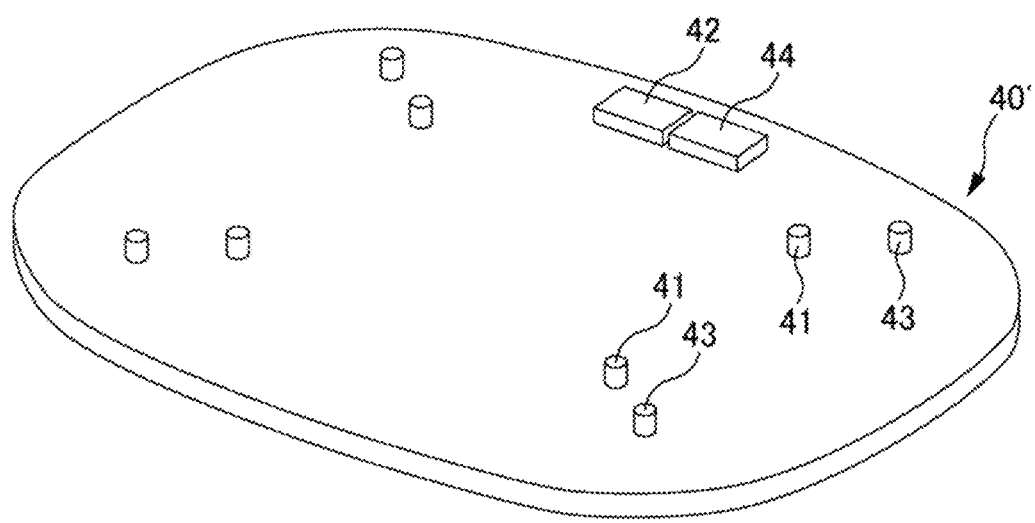
FIG. 8 is a perspective view of a floor plate 40' in a second embodiment.
Figure 9:
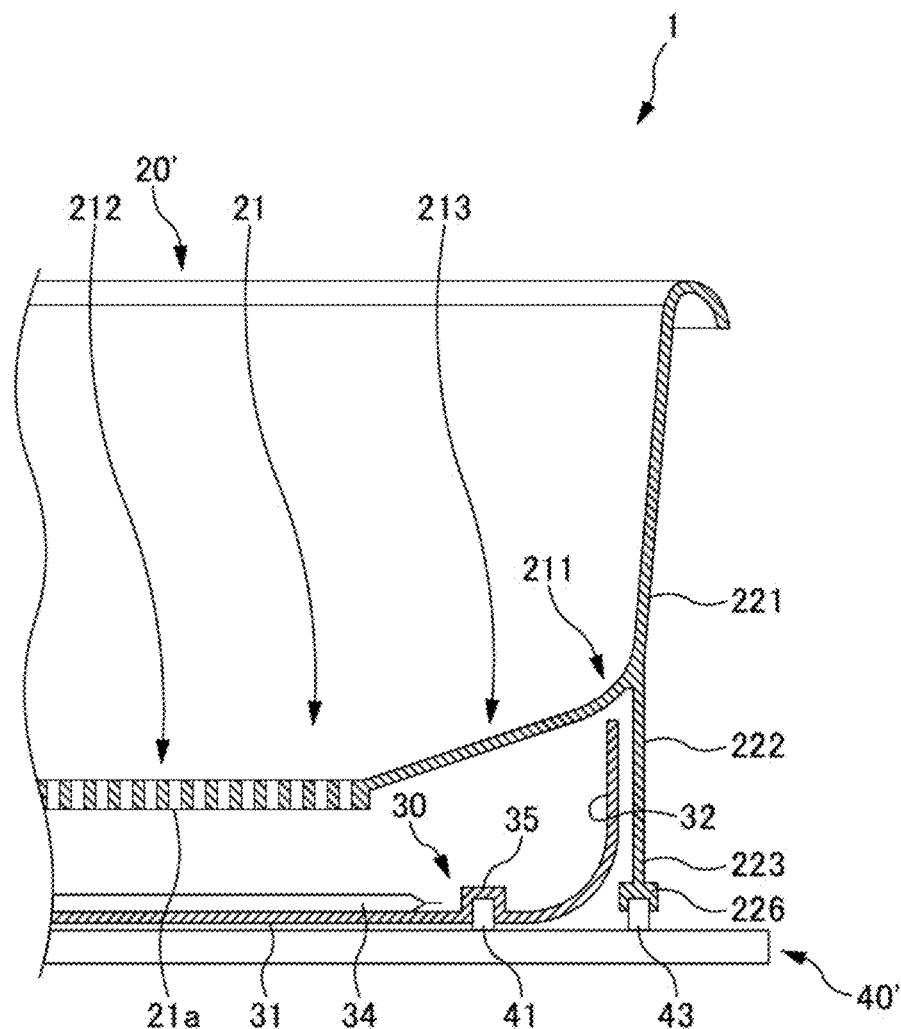
FIG. 9 is a cross-sectional view of a toilet for animal 1 in a second embodiment.

FIG. 8 is a perspective view of a floor plate 40' in the second embodiment. FIG. 9 is a cross-sectional view of the toilet for animal 1 in the second embodiment. FIG. 9 illustrates a cross-section at a position identical to that in FIG. 5 in the first embodiment.

The toilet for animal 1 in the second embodiment includes an upper container 20', the lower container 30, and the floor plate 40'.

The upper container 20' has a configuration approximately similar to that of the upper container 20 in the first embodiment. However, as illustrated in FIG. 9, engaging sections 226 engaged with load cells 43 described later are disposed on the foot portions 223 in the four corners of the upper container 20'.

As illustrated in FIG. 8, the load cell 43 (equivalent to upper-container output unit) and an upper-container control unit 44 are disposed on the floor plate 40' in addition to the load cell 41 and the control unit 42. The load cell 43 and the upper-container control unit 44 are waterproof similar to the load cell 41 and the control unit 42.

The load cell 43 is disposed outside the load cell 41 (specifically, a position facing the engaging section 226 of the foot portion 223 of the upper container 20) on a top surface of the floor plate 40'. Then, when the upper container 20' is located on the floor plate 40', the respective engaging sections 226 of the four foot portions 223 of the upper container 20' are engaged with the load cells 43. Accordingly, the gravity of the upper container 20' acts on only the load cell 43. Then, the load cell 43 outputs a signal (equivalent to upper-container weight signal) that changes according to the weight of the upper container 20'. Thus, in the second embodiment, the load cell 41 and the load cell 43 are disposed on the floor plate 40', thus ensuring increase in the detection objects compared with the first embodiment.

The upper-container control unit 44 has a configuration approximately similar to that of the control unit 42. The upper-container control unit 44 is electrically coupled to the load cell 43 via a signal line (not illustrated). Then, the upper-container control unit 44 detects at least one of the weight of the animal and the amount of feces based on the output signal of the load cell 43.

For example, when the animal steps on the toilet for animal 1 (upper container 20') for excretion, the output signal of the load cell 43 changes. A difference between a value after this change and a value before this change ensures the detection of the weight of the animal. At this time, gravity of the upper container 20' does not act on the lower container 30. Thus, the output signal of the load cell 41 does not change.

The feces of the animal do not pass through the through-holes 21a of the upper container 20'. Thus, the feces of the animal remains on the bottom portion 21 of the upper container 20'. Accordingly, the amount of feces can be detected from a difference between the output signal of the load cell 43 after the animal separates from the toilet for animal 1 (upper container 20') and the output signal of the load cell 43 before the animal steps on the toilet for animal 1 (upper container 20').

The upper-container control unit 44 transmits the above-described result of detection to the display section 26 to cause the display section 26 to display it. Also in the second embodiment, similarly to the first embodiment, the control unit 42 detects the amount of urine based on the output signal of the load cell 41 to cause the display section 26 to display its result of detection. Thus, the second embodiment ensures measurement of the weight of the animal and the amount of feces in addition to the amount of urine. That is, the measurement objects can be increased compared with the first embodiment.

In the present embodiment, the control unit 42 and the upper-container control unit 44 are separately disposed. However, they may be integrally constituted. Then, one control unit may carry out all the processes. In this case, for example, it is known that the animal stepped on the toilet for animal 1, but did not urinate. This ensures detection of a phenomenon specific to a lower urinary tract disease.

As described above, when the fact that the animal stepped on the toilet for animal 1, but did not urinate is detected, another sensor not the load cell 43 may be disposed. For example, a light-emitting section and a light-receiving section of an infrared sensor may be disposed on a position facing an interior upper portion of the sidewall portion 22 of the upper container 20". Also in this case, when the animal steps on the toilet for animal 1 (upper container 20"), it obstructs the infrared. Thus, it is known that the animal comes for the excretion. Combination of this result and the result of detection of the amount of urine ensures the detection of the fact that the animal stepped on the toilet for animal 1, but did not urinate.

OTHERS

The embodiments are intended for easy understanding of the present invention and are not in any way to be construed as limiting the present invention. Needless to say, the present invention may be modified and improved without departing from the scope of the invention, and equivalents thereof are also encompassed by the invention.

In the above-described embodiment, the toilet for animal 1 is a type where the receiving section 31 is disposed on the lower container 30 (a type where the upper container is put on the lower container). However, it is not limited to this. For example, it may be applied to a toilet for animal that is a type where a tray (receiving section) is taken into and out of the lower container.

In the above-described embodiment, the control unit (control unit 42, upper-container control unit 44) and the display section 26 are disposed on the toilet for animal 1. However, it is not limited to this. For example, a control unit and a display section may be disposed on an external terminal (for example, a personal computer, mobile terminal). Then, the output signal of each load cell is transmitted to the external terminal, and thus the external terminal may carry out measurement and display.

In the above-described embodiment, the load cell 41 and the load cell 43 have the circular cylindrical shapes. However, it is not limited to this. For example, the load cell may have another shape such as a sheet shape and an annular shape.

The invention claimed is:

1. A toilet for animal, comprising:
an upper container having a plurality of holes formed on a bottom portion of the upper container, the plurality of holes penetrating in an up-down direction of the upper container;
a lower container including a receiving section for receiving excrement that has passed through the plurality of holes, gravity of the upper container not acting on the lower container; and
an output unit configured to output a signal changing according to an amount of the excrement received by the receiving section,
wherein
the bottom portion has a level plane surface portion,
the plurality of holes is provided in the level plane surface portion, and
an outer shape of each of the plurality of holes has curved portions at two ends in a longitudinal direction of the upper container, as viewed from above.

2. The toilet for animal according to claim 1, wherein
the upper container includes a sidewall portion that constitutes an outer wall of the upper container, and
an average thickness of the level plane surface portion is greater than an average thickness of the sidewall portion.

3. The toilet for animal according to claim 1, further comprising an absorbent sheet configured to absorb the excrement, wherein
the absorbent sheet is configured to be placed on the receiving section.

4. The toilet for animal according to claim 1, wherein the output unit is waterproof.

5. A toilet for animal, comprising:
an upper container having a plurality of holes formed on a bottom portion of the upper container, the plurality of holes penetrating in an up-down direction of the upper container;
a lower container including a receiving section for receiving excrement that has passed through the plurality of holes, gravity of the upper container not acting on the lower container;
an output unit configured to output a signal changing according to an amount of the excrement received by the receiving section; and
a floor plate in which the output unit is provided and that is configured to be installed on a floor,
wherein
the lower container includes
a contact portion in two end portions in a direction orthogonal to a longitudinal direction of the lower container; and
a non-contact portion between the two end portions in the direction orthogonal to the longitudinal direction of the lower container,
the contact portion is a portion that comes into contact with the floor plate, and
the non-contact portion is a portion that does not come into contact with the floor plate.

6. The toilet for animal according to claim 5, wherein
the floor plate includes a control unit configured to detect an amount of the excrement based on the signal outputted from the output unit.

7. The toilet for animal according to claim 6, wherein
the control unit is configured to detect an amount of the excrement each time by calculating a difference between a signal outputted before excretion and a signal outputted after excretion.

8. A toilet for animal, comprising:
an upper container having a plurality of holes formed on a bottom portion of the upper container, the plurality of holes penetrating in an up-down direction of the upper container;
a lower container including a receiving section for receiving excrement that has passed through the plurality of holes, gravity of the upper container not acting on the lower container; and
an output unit configured to output a signal changing according to an amount of the excrement received by the receiving section,
wherein
the upper container includes an extending wall portion that extends downward,
a lower end of the extending wall portion is located below lower ends of the plurality of holes,
the upper container and the lower container are separatable from each other, and
the bottom portion and the extending wall portion are provided in the upper container in not-separable manner.

9. A toilet for animal, comprising:
an upper container having a plurality of holes formed on a bottom portion of the upper container, the plurality of holes penetrating in an up-down direction of the upper container;
a lower container including a receiving section for receiving excrement that has passed through the plurality of holes, gravity of the upper container not acting on the lower container; and
an output unit configured to output a signal changing according to an amount of the excrement received by the receiving section,
wherein
an outer shape of each of the plurality of holes has curved portions in two ends in a longitudinal direction of the upper container, as viewed from above,
the upper container further includes a sidewall portion,
the bottom portion has a plane surface portion that is located lowermost in the up-down direction,
the plane surface portion is level,
a thickness of the plane surface portion is greater than a thickness of the sidewall portion,
the plane surface portion has the plurality of holes formed thereon,
an outer shape of the plane surface portion including two first straight portions, two second straight portions, and four curved portions,
each of the first straight portions extends along the longitudinal direction of the upper container,
each of the second straight portions extends along a transverse direction of the upper container, and
the four curved portions connect ends of each of the two first straight portions and ends of each of the two second straight portions.

10. A toilet for animal, comprising:
an upper container having a plurality of holes formed on a bottom portion of the upper container, the plurality of holes penetrating in an up-down direction of the upper container;

a lower container including a receiving section for receiving excrement that has passed through the plurality of holes, gravity of the upper container not acting on the lower container;

an output unit configured to output a signal changing according to an amount of the excrement received by the receiving section; and an absorbent sheet configured to absorb the excrement and to be placed on the receiving section, wherein the receiving section is capable of being taken into and out of the lower container.

11. A toilet for animal, comprising:

an upper container having a plurality of holes formed on a bottom portion of the upper container, the plurality of holes penetrating in an up-down direction of the upper container;

a lower container including a receiving section for receiving excrement that has passed through the plurality of holes, gravity of the upper container not acting on the lower container;

an output unit configured to output a first signal changing according to an amount of the excrement received by the receiving section; and a control unit configured to output a second signal to cause a display section to display an accumulated amount of the excrement based on the first signal that has been output from the output unit, the display section being provided in a terminal that is different from the toilet.

12. A toilet for animal, comprising:

an upper container having a plurality of holes formed on a bottom portion of the upper container, the plurality of holes penetrating in an up-down direction of the upper container;

a lower container including a receiving section for receiving excrement that has passed through the plurality of holes, gravity of the upper container not acting on the lower container; and an output unit configured to output a first signal changing according to an amount of the excrement received by the receiving section, a control unit configured to output a second signal for calculating an accumulated amount of the excrement based on the first signal that has been output from the output unit.

\* \* \* \* \*